(12) United States Patent
Busch et al.

(10) Patent No.: US 8,144,962 B2
(45) Date of Patent: Mar. 27, 2012

(54) LOCAL MOTION COMPENSATION BASED ON LIST MODE DATA

(75) Inventors: Marc Busch, Aachen (DE); Ralph Brinks, Hagen (DE); Carsten Meyer, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 881 days.

(21) Appl. No.: 12/279,996

(22) PCT Filed: Feb. 5, 2007

(86) PCT No.: PCT/US2007/061597
§ 371 (c)(1),
(2), (4) Date: Aug. 20, 2008

(87) PCT Pub. No.: WO2007/100955
PCT Pub. Date: Sep. 7, 2007

(65) Prior Publication Data
US 2010/0166274 A1   Jul. 1, 2010

Related U.S. Application Data

(60) Provisional application No. 60/777,469, filed on Feb. 28, 2006.

(51) Int. Cl.
G06K 9/00 (2006.01)

(52) U.S. Cl. .......................... 382/131; 378/4

(58) Field of Classification Search .............. 378/4–20; 382/131, 128
See application file for complete search history.

(56) References Cited

U.S. PATENT DOCUMENTS
6,980,683 B2   12/2005   Jones

2005/0123183 A1   6/2005   Schleyer et al.
2006/0178575 A1*  8/2006   Piacsek et al. ............... 600/413

OTHER PUBLICATIONS

Buhler, P., et al.; An Accurate Method for Correction of Head Movement in PET; 2004; IEEE Trans. on Medical Imaging; 23(8)1176-1185.
Jacobs, F., et al.; A fast algorithm to calculate the exact radiological path through a pixel or voxel space; 1998; J. of Computing & Information Technology; 6(1)89-94.
Klein, G. J., et al.; Fine-Scale Motion Detection Using Intrinsic List Mode PET Information; 2001; IEEE; pp. 71-78.
Menke, M., et al.; Compensation Methods for Head Motion Detected During PET Imaging; 1996; IEEE Trans. on Nuclear Science; 43(1)310-317.
Rahmim, A.; Advanced Motion Correction Methods in PET; 2005; 17 pages.
Visvikis, D., et al.; A posteriori respiratory motion gating of dynamic PET images; 2003; Nuclear Science Symposium Conf. Record IEEE; vol. 5;pp. 3276-3280.
Bruyant, P. P., et al.; Correction of the Respiratory Motion of the Heart by Tracking of the Center of Mass of Thresholded Projections: A Simulation Study Using the Dynamic MCAT Phantom; 2002; IEEE Trans. on Nuclear Science; 49(5)2159-2166.
Yamamoto, M., et al.; Effect of the Software Coincidence Timing Window in Time-of-Flight Assisted Positron Emission Tomography; 1983; IEEE Trans. on Nuclear Science; 30(1)711-714.

* cited by examiner

Primary Examiner — Hoon Song

(57) ABSTRACT

A method for locally correcting motion in an image reconstructed by a reconstruction system (42) of an imaging system (10) with raw data includes estimating a characteristic feature of a region of interest within the reconstructed image from the raw data, correcting the raw data associated with the region of interest for motion with the estimated region characteristic feature, and reconstructing a motion-corrected image corresponding to the region of interest with the corrected raw data.

32 Claims, 5 Drawing Sheets

LOCAL MOTION COMPENSATION BASED ON LIST MODE DATA

CROSS REFERENCE TO RELATED APPLICATIONS

This application claims the benefit of U.S. provisional application Ser. No. 60/777,469 filed Feb. 28, 2006, which is incorporated herein by reference.

The following relates to medical imaging systems. It finds particular application to motion compensation in PET imaging, but is also applicable to other modalities of diagnostic imaging.

Anatomical motion is a known problem in medical imaging (e.g., Positron Emission Tomography (PET), Single Photon Emission Computed Tomography (SPECT), Computed Tomography (CT), Magnetic Resonance Imaging (MR), etc.). The lungs and other portions of the anatomy undergo cyclic movement with patient breathing, the cardiac cycle, and the like. Such movement during data acquisition results in motion-averaged (e.g., blurred) images, which tend to have low image quality and limited quantification capabilities (e.g., reduced contrast, decreased lesion detectability, worsened standardized uptake value (SUV) quantitation, etc.).

One technique used to reduce motion artifact is to have the patient hold their breath during data acquisition. However, in some instances the acquisition time is too long for the patient to hold their breath during the entire data acquisition.

With gated acquisition, events are sorted into specific time bins depending on the present breathing state of the patient, which is either measured with external sensors or directly extracted from the acquired data. The separate bins or gates are then reconstructed separately to give images with less motion artifact. However, the decreased count statistics of these images leads to increased noise and hinders accurate quantification. In addition, many clinical applications do not require motion compensation over the entire image. For example, in oncology studies clinicians are often only interested in quantifying the SUV and size of lung lesions.

Conventional active motion correction schemes (e.g., deformation model) can be very complex and time-consuming, and prone to errors. Furthermore, they typically require additional input about the breathing state of the patient over time, which needs to be acquired with external sensors.

In one aspect, a method for correcting motion in an image reconstructed by a reconstruction system of an imaging system with raw data is illustrated. The method includes estimating a characteristic feature of a region of interest within the reconstructed image from the list mode data. The raw data associated with the region of interest is then corrected for motion with the estimated region characteristic feature. A motion-corrected image corresponding to the region of interest with the corrected raw data is then reconstructed.

One advantage includes facilitating correcting for motion artifact in an image.

Another advantage lies in using the data employed to reconstruct an image to correct for motion in that image.

Another advantage resides in eliminating the need for physical motion detectors and complex motion correction algorithms.

Still further advantages will become apparent to those of ordinary skill in the art upon reading and understanding the detailed description of the preferred embodiments.

The drawings are only for purposes of illustrating embodiments and are not to be construed as limiting the claims.

Figure 5:
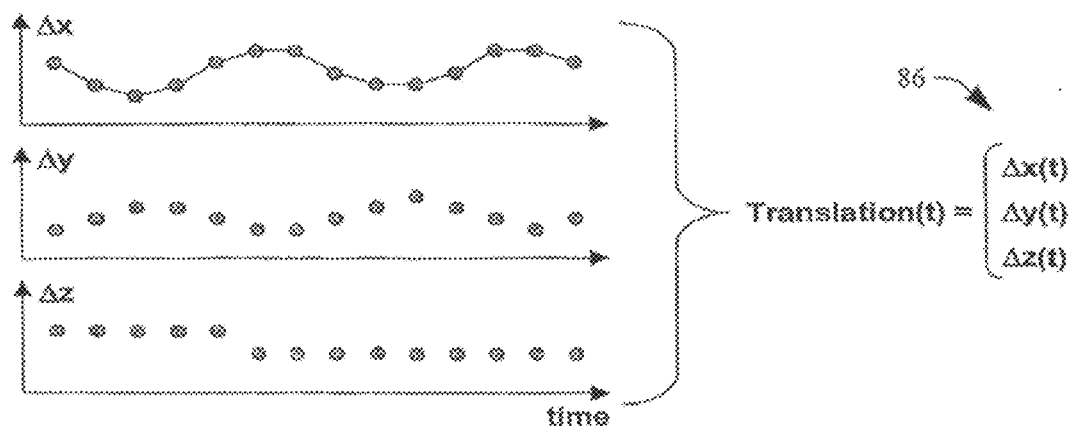

FIG. 5 graphically illustrates information about the position of the center of mass for each time partial image in which values in between can be interpolated to generate a smooth translation offset with time.

Figure 6:
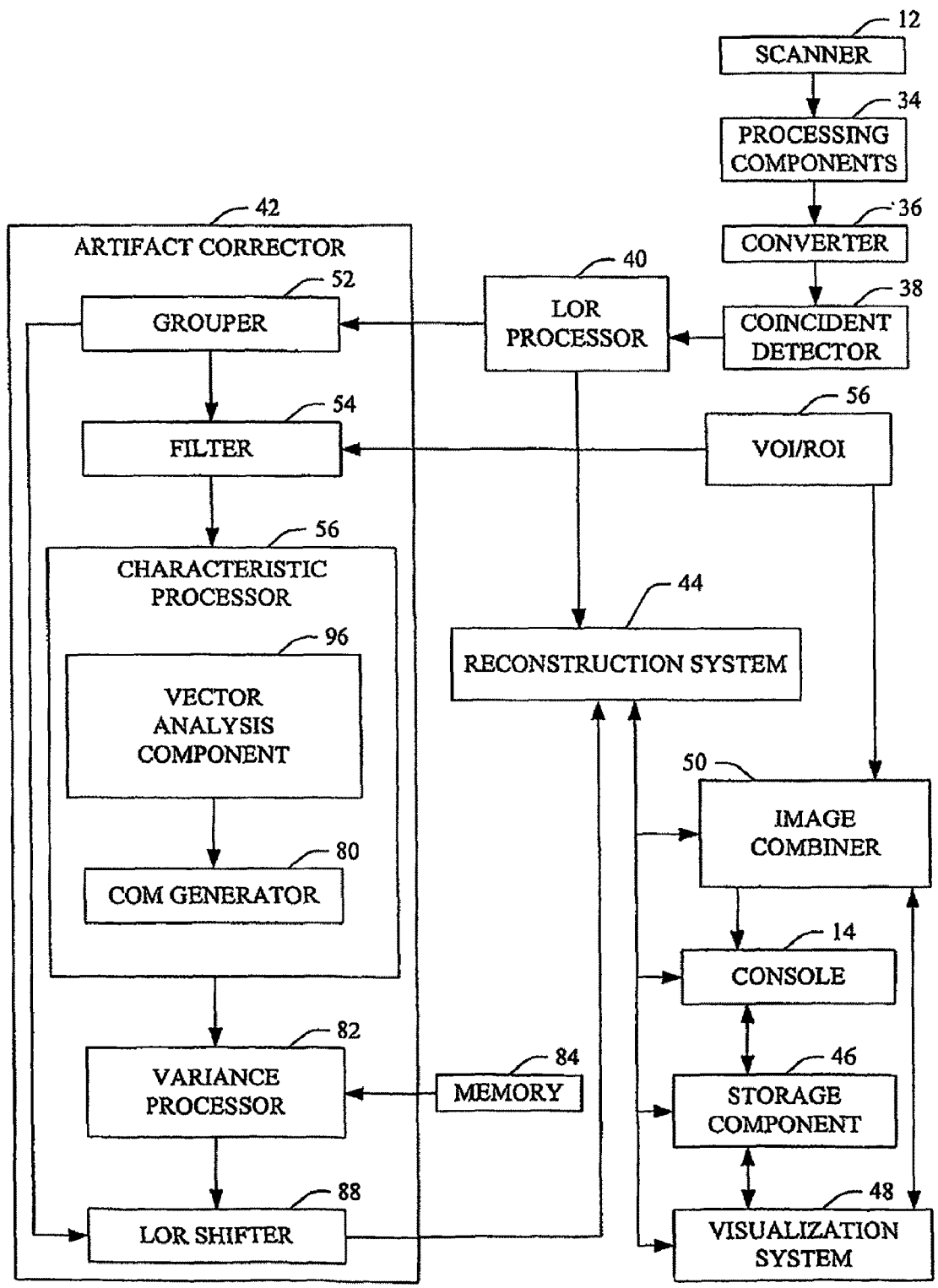

FIG. 6 illustrate another exemplary technique for correcting motion within an image in which vector analysis is used to correct LORs.

Figure 7:
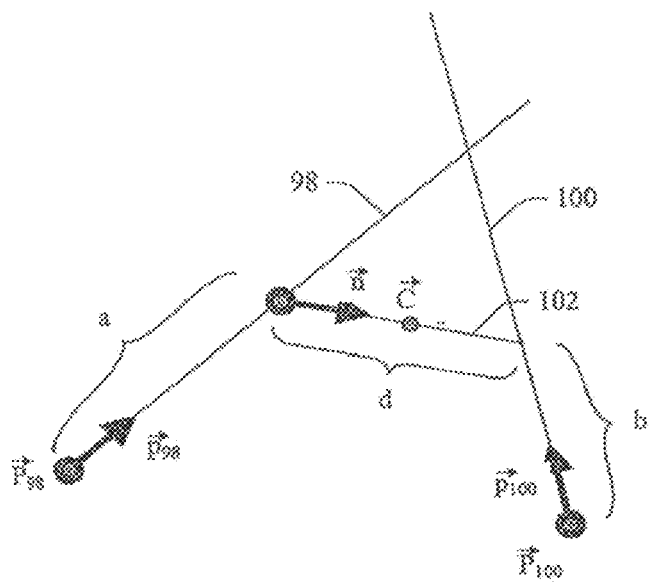

FIG. 7 illustrates an exemplary vector approach for determining an estimate for the center of mass.

Figure 8:
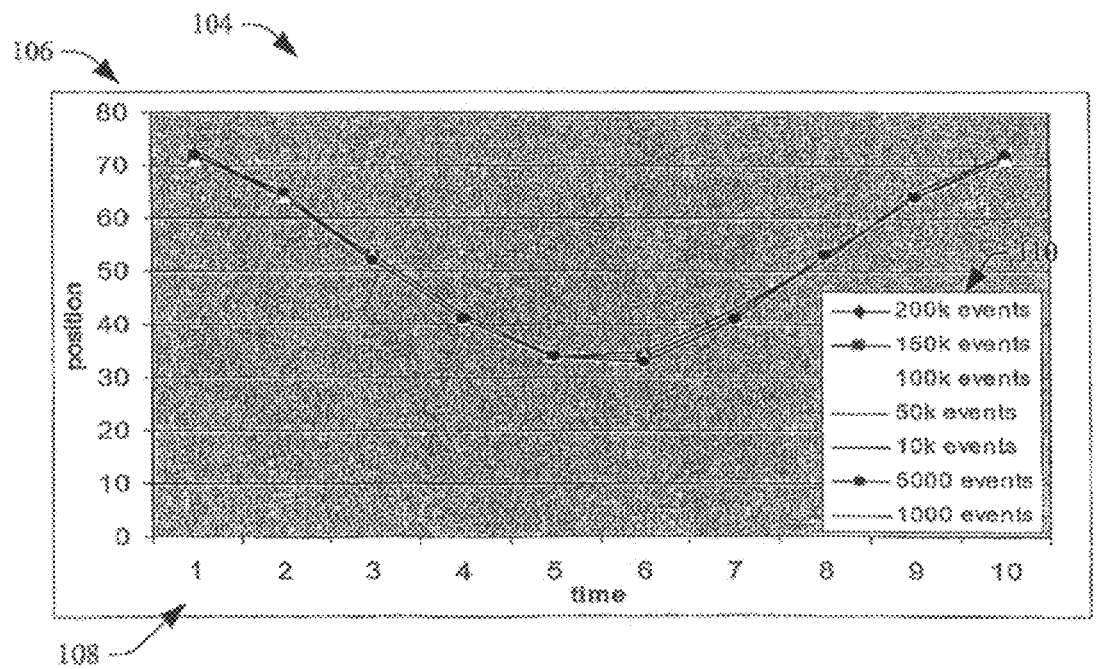

FIG. 8 illustrates exemplary results for simulated list mode data of a moving sphere.

Figure 1:
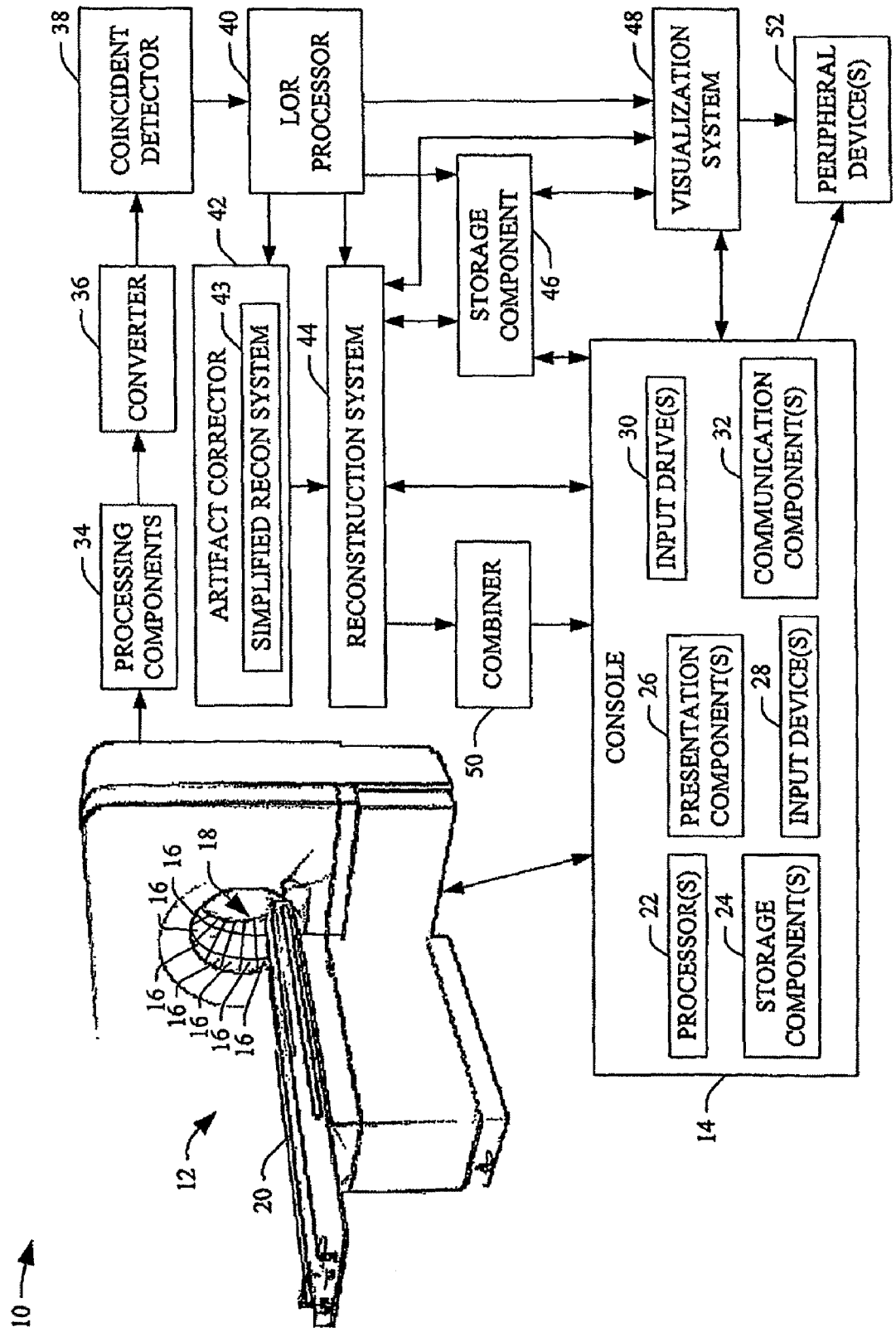
FIG. 1 illustrates a medical imaging system having components that correct for motion with the data used to reconstruct images.

FIG. 1 illustrates a medical imaging system 10 that includes a scanning system 12 and a console 14 that controls the scanning system 12, presents reconstructed images, and provides visualization and data/image correction tools. The scanning system 12 can be any type of medical imaging scanner including one or more of a Positron Emission Tomography (PET) scanner, a Single Photon Emission Computed Tomography (SPECT) scanner, a Computed Tomography (CT) scanner, a Magnetic Resonance Imaging (MR) scanner, a PET/CT scanner, etc. For this example, the scanning system 12 is a PET scanner. As such, the scanning system 12 includes a plurality of radiation detector modules 16 (e.g., hundreds, thousands, etc.), each arranged around an imaging region 18. The modules 16 are positioned or rotated to define one or more rings (e.g., two, ten, a hundred, etc.) of radiation detectors along an axial direction that detect radiation events (e.g., gamma rays) occurring within the imaging region 18. The scanning system 12 also includes a support mechanism 20 for positioning a subject (e.g., a human) in the imaging region 18 before, during and/or after imaging. The support mechanism 20 may be linearly movable in an axial direction generally transverse to the radiation detectors 16.

The console 14 is a microprocessor-based system (e.g., a mainframe, a workstation, a desktop, a laptop, etc.). As such, the console 14 includes at least one or more processors 22, storage components 24 (e.g., volatile and non-volatile, resident and portable memory, etc.), presentation components 26 (e.g., a flat panel monitor, a liquid crystal display (LCD), a cathode ray tube (CRT) monitor etc.), input devices 28 (e.g., a mouse, a keyboard, a keypad, a roller ball, a digital pen, a microphone, a touch screen, tape drive, disk drive, etc.), input drives 30 (e.g., DVD, CD, magnetic disk, optical disk, tape, etc.), wire and/or wireless communication components 32 (e.g., Ethernet, USB, serial, parallel, FireWire, etc.), as well as various other computer related components.

The console 14 is used to plan patient procedures (e.g., provide for selecting imaging protocol(s), suitably setting imaging parameters, etc.), commence scanning with the scanning system 12, present reconstructed images, and provide various visualization and data/image correction capabilities, as well as other functions such terminating procedures, transferring data, positioning the support mechanism 20, etc.

Examples of suitable visualization capabilities, include but are not limited to, forming three dimensional volumes from a two dimensional data sets, defining primitives (e.g., regions and/or volumes of interest), measuring various image quality statistics, superimposing images obtained through different modalities, removing anatomy and/or a defined region/volume of interest from within an image, etc. As discussed in detail below, these visualization capabilities are leveraged to facilitate removing motion artifact from various regions (e.g., one or more regions or volumes of interest, etc.) in an image through one or more motion estimation/correction algorithms executed by the one or more processors 22. These algorithms use the data (e.g., list mode data) employed to reconstruct images to correct the motion within the reconstructed images.

In preparation for imaging with the scanning system 12, a radiopharmaceutical is administered to the subject, and the subject is suitably positioned within the imaging region 18. The radiopharmaceutical undergoes radioactive decay, which results in an emission of a positron. The positron interacts with one or more nearby electrons and annihilates, which produces two oppositely directed gamma rays having energies of about 511 keV each. The two oppositely directed gamma rays strike opposing detector modules 16 concurrently at substantially the same time. Since positions not originating equidistant from a pair of detectors travel different distances, there is a time offset between coincident events.

A typical detector module 16 includes one or more scintillation crystals (not shown). Each scintillation crystal produces a scintillation of light when struck by a radiation event such as a gamma ray produced from positron annihilation. The light produced by each crystal is received by one or more photodetectors (not shown) such as photomultiplier tubes. Each of the photodetectors converts the light into a representative electrical signal. Solid state detectors which generate the electrical signals directly in response to receiving radiation and other types of detection systems are also contemplated. The resulting electrical signal from the one or more photodetectors are conveyed and processed by one or more processing components 34. Suitable processing by the processing components 34 includes signal amplification, filtering, and/or conditioning. The processed electrical signals are then conveyed to a converter 36, which digitizes and time stamps the signals. Buffers and/or other storage medium (not shown) can be used to facilitate pre-processing and digitizing the signals.

The data is then conveyed to a coincident detector 38 that identifies pairs of substantially simultaneous coincident gamma ray detections, which correspond to electron-positron annihilation event pairs. This processing can include, for example, energy filtering (e.g., discarding radiation detection events outside of a selected energy filtering window disposed about 511 keV) and/or coincidence filtering (e.g., discarding radiation detection event pairs temporally separated from each other by greater than a selected time filtering interval or more than two events within a common window, random coincidence identification using a delayed windowing technique, etc.). Upon identifying coincident event pairs, a line of response (LOR) processor 40 processes the spatial information for each pair of events to identify a spatial LOR that connects gamma ray detections in each pair. Since the two gamma rays emitted by a positron-electron annihilation event are oppositely spatially directed, the electron-positron annihilation event is known to have occurred somewhere on the LOR. In time-of-flight (TOF) PET, the processor 40 analyzes a difference between the detection times of the pair of gamma rays to determine a segment along the LOR along which the annihilation event occurred.

Figure 2:
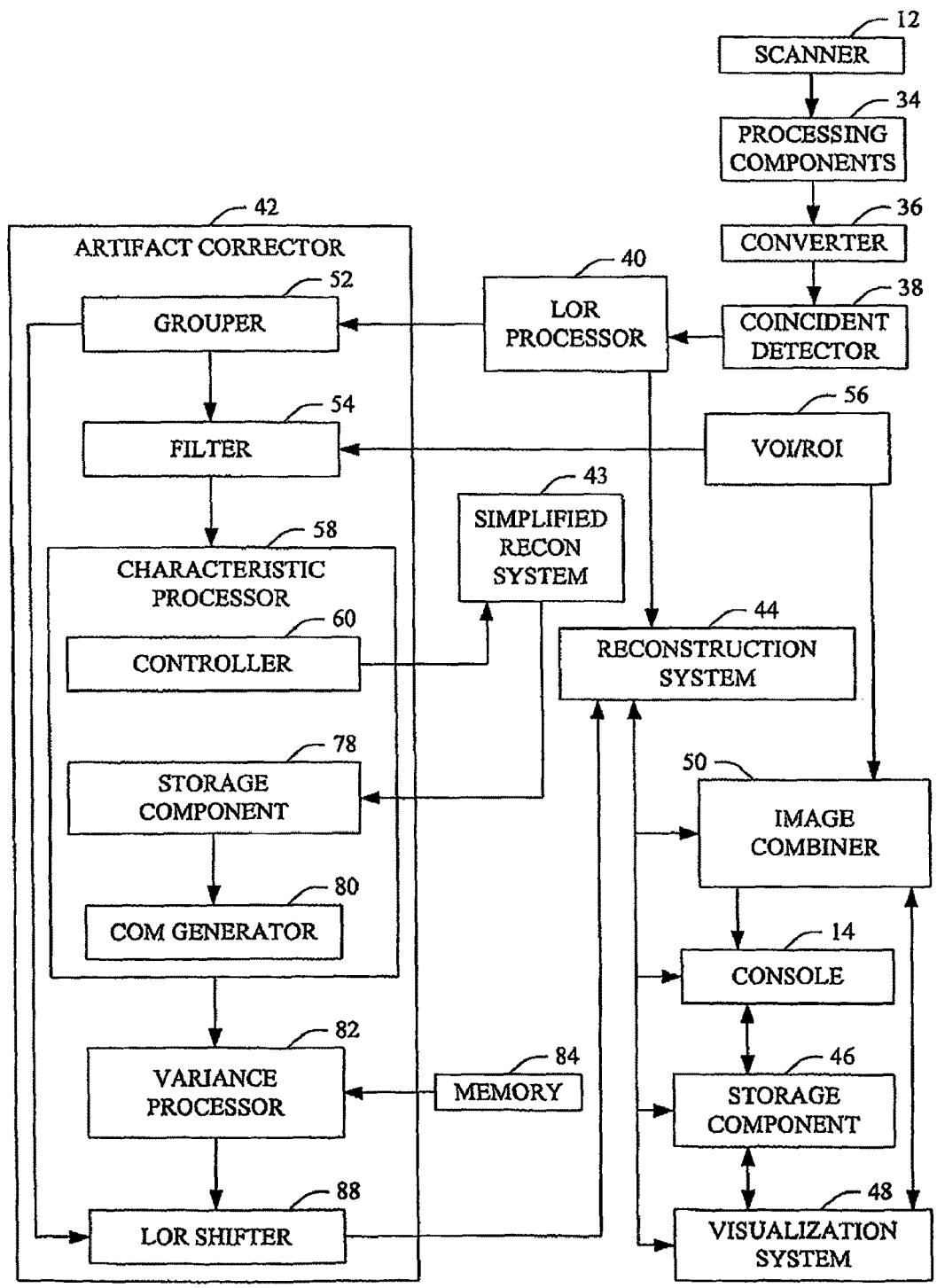
FIG. 2 illustrate an exemplary technique for correcting motion within an image in which groups of LORs are shifted by a corresponding motion correction offset and then reconstructed to generate a motion corrected image.

The spatial LOR and/or the pairs of coincident events are conveyed to an artifact corrector 42 (which is described in greater detail below) that is associated with a simplified reconstruction system 43 (which can be part of the artifact corrector 42 as depicted here or external to the artifact corrector 42 as depicted in FIG. 2 below) that at least facilitates motion correcting the LORs, a reconstruction system 44, a storage component 46, and/or a visualization system 48. The reconstruction system 44 reconstructs one or more images from this data using any suitable reconstruction algorithm. Examples of suitable algorithms include, but are not limited to, filtered backprojection and/or iterative backprojection with or without correction. Because the motion correction might artifact areas of the image outside the region of interest, in one embodiment an image combiner 50 replaces the ROI of a non-corrected image with the ROI from the motion corrected image.

The resulting reconstructed images and/or raw data can be conveyed to the console 14 and stored in the one or more of the storage components 24 and/or presented to the user via the one or more presentation components 26. Additionally or alternatively, the resulting reconstructed images can be conveyed to the storage component 46. In this instance, the console 14 can obtain the reconstructed images and/or raw data from the storage component 46. Additionally or alternatively, the reconstructed images and/or raw data can be conveyed to the visualization system 48 from the console 14, the reconstruction system 44, and/or the storage component 46. Both the console 14 and the visualization system 48 can send data and/or images to one or more peripheral devices 52, including a filmer, a printer, a plotter, a facsimile, an email address, a computer, a network, etc.

As briefly discussed above, the console 14 provides various visualization and data/image correction capabilities. Thus, as images are being sent to the console 14 during and/or after a scanning procedure, the clinician can employ the visualization and data/image correction capabilities to view and/or correct for image artifacts (e.g., motion artifact). Such capabilities can be part of the system software and/or applications stored in the storage components 24 and executed by the processors 22. Additionally or alternatively, the visualization system 48 can be used to facilitate real-time and/or post-processing artifact correction. The visualization system 48 may be a dedicated processing system with specialized hardware (not shown) such as graphics engines, graphics accelerators, larger quantities of memory, higher powered processors, high resolution monitors, etc. and/or specialized software applications that facilitated complex and time intensive image processing algorithms. In an alternative embodiment (not shown), the console 14 and the visualization system 48 are combined into a single unit to provide scanner control as well as advanced image processing capabilities.

Examples of suitable techniques for correcting motion artifact are described next. However, it is to be appreciated that other techniques as well as derivations of the techniques described herein are also contemplated. Moreover, the motion artifacted image and the motion corrected image can be reconstructed concurrently or the motion artifacted image can be reconstructed first and motion corrected images corresponding to one or more ROI/VOIs can be reconstructed subsequently. A first technique (presented below in FIG. 2) uses a simplified Siddon based algorithm, and another technique (presented below in FIG. 6) uses a vector space approach.

Referring initially to FIG. 2, the LOR processor 40 conveys the remaining LORs to a grouper 52 of the artifact corrector 42. The grouper 52 divides the LORs into groups that span about 100 milliseconds, for example. In one instance, the time span can be fixed and the number of LORs per group can vary. In another instance, the number of LORs can be fixed to about 10000, for example, and the time span can vary. In yet another instance, both the number and time span can be thresholded or otherwise both be allowed to vary, within constraints. A filter 54 filters out the LORs that do not intersect a user or automatically defined volume of interest/region of interest (VOI/ROI) 56. In the case of TOF PET, LORs that intersect the volume of interest, but whose segment identifying the possible location of the annihilation event falls outside of VOI/ROI 56 are also eliminated.

Figure 3:
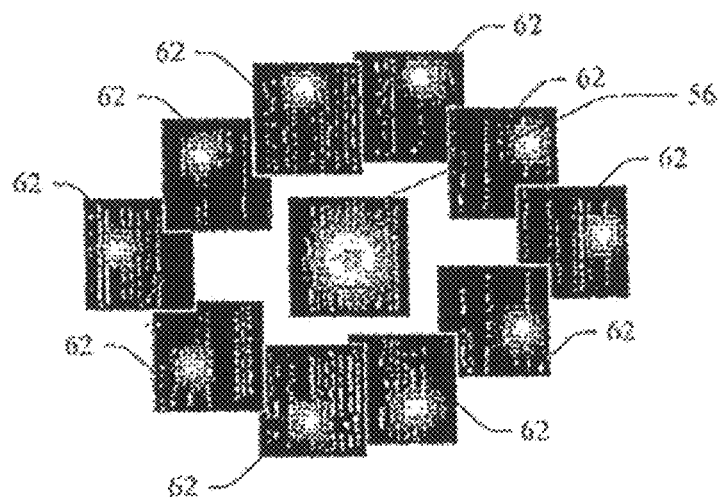
FIG. 3 illustrates a graphical example of a plurality of exemplary intermediate images, derived from a VOI/ROI, that are used to determine the motion correction offset.

A characteristic processor 58 determines a characteristic feature such as the center of mass or other center function of the LORs of each group. In this example, a controller 60 of the characteristic processor 58 accesses the simplified reconstruction system 43 to reconstruct each group of LORs into a partial image. FIG. 3 illustrates a graphical example of the VOI/ROI 56 and a plurality of exemplary intermediate images 62 derived from the VOI/ROI 56 by the simplified reconstruction system 43. Ten intermediate images 62 are illustrated; however, in other embodiments, more intermediate images can be generated.

Figure 4:
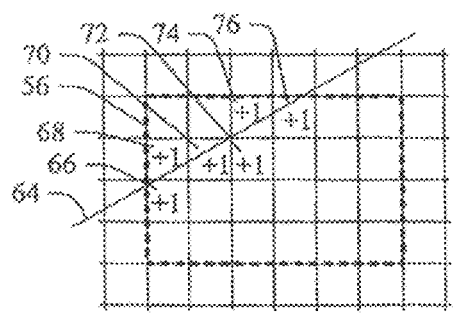
FIG. 4 illustrates an exemplary technique for facilitating generating intermediate images.

In one simplification, the exact overlap length of each LOR with each voxel is not calculated. Instead, the voxel values inside the VOI/ROI 56 are increased by one for each voxel that is intersected by the LOR for each of the intermediate images 62. This is illustrated in FIG. 4, wherein a LOR 64 intersects voxels 66, 68, 70, 72, 74 and 76 within the VOI/ROI 56. As depicted, the value of each of the voxels 66-76 is increased by one. This simplified back projection is computationally efficient as the number of required divisions and multiplications is minimal. The time for generating a sufficient number of intermediate images 62 typically is in the order of a few seconds.

Returning to FIG. 2, the partial images are stored in a storage component 78. A center of mass (COM) generator 80 computes a center of mass or other characteristic feature of each partial image stored in the storage component 78. Coincidences from outside the VOI/ROI 56 that are associated with LORs that hit the VOI/ROI 56, contribute to the intermediate images 62. Thus, the locally constrained back projection described above may have a significant background from events outside the VOI/ROI 56. To minimize the impact of this background, the data is thresholded such that only voxels with values above about 50% (or other percentage deemed suitable by the clinician) of the maximum ROI/VOI value are considered in the calculation of the center of mass.

A variance processor 82 determines a translational offset or other deviation between a center of mass or other characteristic feature of a current group of LORs and a pre-selected center of mass or other characteristic feature stored in a memory 84. The pre-selected center can be set as the center of mass of a first group processed, a motion artifacted image, or the like or can be operator selected. The deviation of each center of mass is stored in a vector, an array, a string, a matrix, and the like. FIG. 5 graphically illustrates information about the position of the center of mass for each time partial image. The overall center of mass deviations for the full time range is used to calculate a time dependent translation vector 86.

Returning to FIG. 2, a LOR shifter 88 corrects the list mode data for motion by shifting each LOR or each group of LORs in the original data set by an amount given by the deviation (e.g., the translation vector 86) to get a motion corrected list mode dataset. This is done at the full timing resolution of the list mode dataset, unlike conventional gating techniques in which the data is still averaged or smeared over the duration of each time frame. This correction can also be integrated as part of a real time image reconstruction. It is assumed that deformation of the tissue inside the ROI/VOI can be neglected, so that the motion of the center of mass reflects the motion of the tissue inside the ROI/VOI. This assumption is reasonable for small VOIs. Although described based on translation, other connections are also contemplated, such as rotational, elasticity, and the like.

The shifted or otherwise deviation corrected LORs along with translated or non-translated LORs from outside the VOI/ROI are then reconstructed by the reconstruction system 44. Because the LORs have all been shifted to the target center of mass, the reconstructed image of the region of interest is motion corrected. In one instance, the resulting corrected image and an uncorrected image are presented by the presentation component 26 of the console 14 in different display windows. In another instance, the data is motion corrected and reconstructed in substantially real time as it is read out of the scanner. As each additional group of LORs becomes part of the displayed image, the display image builds progressively sharper. In yet another instance, a portion of the corrected image is spliced into the corresponding region of a larger uncorrected image. The various images, combinations of images and/or derivations thereof are presented by the presentation component 26 of the console 14. In yet another instance, the motion corrected image is provided to the storage component 46 and/or the visualization system 48.

In the embodiment illustrated in FIG. 6, the characteristic processor 56 alternatively determines a center of mass for the LORs with a vector analysis component 96. As described above, the LOR processor 40 provides the LORs to the artifact corrector 42. The grouper 52 of the artifact corrector 42 divides the LORs into one or more groups. The filter 54 filters out the LORs outside of the VOI/ROI 56 and, in the case of TOF PET, the LORs that intersect the volume of interest, but whose segment identifying the possible location of the annihilation event falls outside of VOI/ROI 56.

The filtered LORs are provided to the vector analysis component 96. For this example, assume that each LOR in the list mode emission data is defined by a point $\vec{P}_x$ on a LOR and a unit vector $\vec{p}_x$ pointing in the direction of the LOR. FIG. 7 illustrates two such LORs in which a first LOR 98 is associated with a point $\vec{P}_{98}$ and a unit vector $\vec{p}_{98}$ pointing in the direction of the LOR 98, and a second LOR 100 is associated with point $\vec{P}_{100}$ and a unit vector $\vec{p}_{100}$ pointing in the direction of the LOR 100.

The point $\vec{C}$ represents the center point of the shortest line segment 102 connecting the LORs 98 and 100. $\vec{C}$ is defined by:

$$\vec{C} = \vec{P}_{98} + b \cdot \vec{p}_{98} - \frac{d}{2}\vec{n},$$

wherein d is the length of the line segment connecting the LORs 98 and 100 and is defined by:

$$d = |(\vec{P}_{98} - \vec{P}_{100}) \cdot \vec{n}|,$$

wherein n is a unit vector pointing in the direction of the line segment connecting the LORs 98 and 100 and is defined by:

$$\vec{n} := \vec{p}_{98} \times \vec{p}_{100} / |\vec{p}_{98} \times \vec{p}_{100}|,$$

and b is defined by:

$$\left[P_{98}^y - P_{100}^y + dn^y + (P_{100}^x - P_{98}^x - dn^x)\frac{p_{98}^y}{p_{98}^x}\right] \bigg/ \left(p_{100}^y - \frac{p_{100}^x p_{98}^y}{p_{98}^x}\right),$$

wherein superscripts x and y denote the x and y components of the corresponding vector.

Returning to FIG. 6, using this formalism the vector analysis component 96 generates a collection of points {C1, . . . , Cn} for a given number of n successive pairs of LORs from the list mode data. The center of mass generator 80 uses this information to determine the center of mass of this point cloud, which is an estimate of the center of mass of the activity distribution in the specified ROI/VOI. The above technique can be improved by eliminating outliers of the point cloud. Parallel LORs or LORs perpendicular to the x-axis (i.e., $p_0^x$=0), are treated separately. FIG. 8 illustrates exemplary results for simulated list mode data of a moving sphere. The results are graphically presented in a plot 104 illustrating position at a first axis 106 and time at a second axis 108. For this example, list mode data was simulated for an active sphere (r=1 cm) moving with a ±2 cm amplitude. The numbers of events specified at 110 were used to determine the position of the sphere over time directly from the list mode data.

Returning to FIG. 7, the variance processor 82 determines a suitable translation function or other deviation between the current group of LORs and the pre-selected center of mass stored in the memory 84. The LOR shifter 88 adjusts the LORs with the offset or other deviation. The adjusted or otherwise deviation corrected LORs along with translated or non-translated LORs from outside the VOI/ROI are then reconstructed by the reconstruction system 44. Similarly, since the LORs have all been shifted to the target center of mass, the reconstructed image of the region of interest is motion corrected. The motion corrected image is then provided to the console 14, the storage component 46, and/or the visualization component 48.

In one application, the clinician is interested in quantitative values (e.g., for a specific lung lesion). In this instance, the clinician manually defines a region or volume of interest by contouring (via the one or the input devices 28) a geometric primitive on the image presented by the one or more presentation components 26. For instance, the clinician can draw a primitive that encapsulates a substantial portion of a subject lesion. Depending on a preference(s) of the clinician and/or an attribute(s) (e.g., size, shape, relative position, etc.) of the lesion, the primitive may be a square, a rectangle, a circle, an ellipse, a free hand shape, a sphere, a cube, etc., and/or any other two or three dimensional shapes that the console 14 and/or the visualization system 46 provides for region or volume of interest definition.

Alternatively, an algorithm can be utilized to automatically define one or more such regions or volumes of interest. For example, based on a range of values (e.g., defined by the clinician or predefined) that correspond to the grey scale values of the lesion, the executing software can threshold image pixel (or voxel) values and trace a region that includes data within the range. This may result in automatic contouring of a "hot spot," or region of relatively higher emission of radiation, in the image. Similarly, the shape of this primitive may be based on known geometric shapes or irregular in shape. Where multiple imaging modalities are used, the region or volume of interest can be defined on an image generated with data from one modality and this image can be registered to an image generated with data from a different modality. For example, in instances where PET/CT are combined, the clinician can define the region of interest in the CT image, and the CT image can subsequently be registered to the PET image.

Extensions to the foregoing techniques include the following. If time-of-flight (TOF) information is available, it can be exploited to improve motion estimation. In addition, the number of time steps, i.e. the temporal resolution of motion estimation could be adjustable via the graphical user interface (GUI). Further, the number of events used for the estimation of the centre of mass could be adjustable via the GUI. Alternatively, an algorithm can determine the optimal setting for these parameters. In addition, the foregoing techniques can be used for various applications including quantification of lung lesions or the staging of lung tumors or other applications in which localized objects are quantified (e.g., size and absolute activity concentration) under respiratory, cardiac or patient motion.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for correcting motion in an image reconstructed from raw data, comprising:
    identifying a plurality of intermediate region of interest images from segments of the raw data for a number of short time frames;
    adjusting, for each of the plurality of intermediate region of interest images, a voxel value for one or more voxels that reside inside each intermediate region of interest and that intersect a corresponding line of response;
    computing a characteristic feature for each of the intermediate region of interest images;
    computing a difference between each characteristic feature and a selected characteristic feature;
    computing a motion correction vector based on the differences;
    correcting the raw data motion correction vector; and
    reconstructing a motion-corrected image corresponding to the region of interest with the corrected raw data.

2. The method as set forth in claim 1, wherein the characteristic feature is a center of mass.

3. The method as set forth in claim 2, further including:
    removing voxels with values less than a predetermined percentage of a maximum region of interest value before the estimation of the center of mass to decrease the influence from coincidences outside the region of interest.

4. The method as set forth in claim 1, wherein the raw data is list mode data.

5. The method as set forth in claim 1, wherein the region of interest is less than a field of view and localized to anatomy of interest.

6. The method as set forth in claim 1, further including:
    replacing an uncorrected region of interest within a motion artifacted image with the motion-corrected region of interest.

7. The method as set forth in claim 1, further including concurrently presenting the motion-corrected region of interest and an uncorrected image in separate displays.

8. The method as set forth in claim 1, wherein the motion correction vector includes a motion correction translation vector and further including:
correcting the raw data for motion by shifting lines of response in the original data by an amount given by the motion correction translation vector.

9. The method as set forth in claim 1, wherein correcting the raw data includes:
dividing the raw data into groups;
determining a location of the characteristic feature in each group from data in each group;
determining a deviation between the location of the characteristic feature in each group and the estimated characteristic feature;
adjusting the raw data in accordance with the determined deviations.

10. The method as set forth in claim 9, wherein the raw data includes a plurality of lines of response (LORs) and the adjusting step includes:
translating the lines of response in accordance with determined deviations to align the characteristic features of the groups.

11. The method as set forth in claim 1, further including at least one of the following to improve the motion correction:
using time-of-flight information to facilitate estimating motion;
adjusting a temporal resolution to affect the motion correction vector;
adjusting a number of events used for an estimation of the characteristic feature; and
employing an algorithm that determines an optimal setting for one or more parameters.

12. A non-transitory computer readable medium which carries software for controlling one or more processors to execute the method of claim 1.

13. A medical imaging system comprising:
a processor configured to receive the raw data and being programmed to perform the method of claim 1; and
a display connected with the processor, the display displays the reconstructed motion-corrected image corresponding to the region of interest with the corrected raw data.

14. A method for correcting motion in an image reconstructed from raw data:
estimating a characteristic feature of a region of interest within the reconstructed image from the raw data;
computing a vector that represents a center point of a shortest line segment connecting a pair of lines of response in the raw data;
correcting the raw data associated with the region of interest for motion with the computed vector; and
reconstructing a motion-corrected image corresponding to the region of interest with the corrected raw data.

15. The method as set forth in claim 14, wherein the vector includes a collection of points for a given number of successive pairs of lines of response.

16. The method as set forth in claim 14, wherein the vector is computed as a function of $$\vec{C} = \vec{P}_0 + b \cdot \vec{p}_0 - \frac{d}{2}\vec{n},$$

wherein $\vec{P}_0$ and $\vec{P}_1$ are points on a pair of lines of response and $\vec{p}_0$ and $\vec{p}_1$ are the unit direction vectors for these lines of response, d is a length of the shortest line segment connecting the lines of response and is defined by $d = |(\vec{P}_0 - \vec{P}_1) \cdot \vec{n}|$, wherein n is a unit vector pointing in the direction of the shortest connection and is defined by $\vec{n} := \vec{p}_0 \times \vec{p}_1 / |\vec{p}_0 \times \vec{p}_1|$, and b is defined by $$b = \left[P_0^y - P_1^y + dn^y + (P_1^x - P_0^x - dn^x)\frac{p_0^y}{p_0^x}\right] / \left(p_1^y - \frac{p_1^x p_0^y}{p_0^x}\right),$$

wherein superscripts x and y denote the x and y components of the corresponding vector.

17. The method as set forth in claim 14, further including computing a center of mass of the distribution in the region of interest.

18. The method as set forth in claim 17, further including:
correcting the raw data for motion by shifting lines of response in the original data in accordance with the center of mass movement.

19. The method as set forth in claim 14, further including refining the result by ignoring data outside of the region of interest.

20. A non-transitory computer-readable medium that stores instructions for controlling one or more processors to perform the method of claim 14.

21. A medical imaging system that corrects motion in a reconstructed image with data used to reconstruct the image, comprising:
a plurality of detectors that detect electron-positron annihilation events;
a coincident detector that identifies pairs of substantially simultaneous coincident events within the electron-positron annihilation events;
a line of response processor that processes the events and identifies lines of responses that connect events within each coincident event pair; and
one or more processors programmed to:
estimate a characteristic feature of a region of interest within the reconstructed image from the raw data;
compute a vector that represents a center point of a shortest line segment connecting a pair of lines of response in the raw data;
correct the raw data associated with the region of interest for motion with the computed vector; and
reconstruct a motion-corrected image corresponding to the region of interest with the corrected raw data.

22. The medical imaging system as set forth in claim 21, wherein the region of interest is localized to less than a field of view of the medical imaging system.

23. The medical imaging system as set forth in claim 21, wherein the processing components execute one of a simplified Siddon based algorithm and a vector based algorithm facilitate estimating a center of mass for the region of interest.

24. The medical imaging system as set forth in claim 21, further including:
presentation components which present at least one of:
the motion corrected image,
concurrent displays of the motion corrected image and a non-corrected image, and
a non-corrected image with the motion corrected region of interest substituted for the corresponding region of interest of the non-corrected image.

25. A medical imaging system that corrects motion in a reconstructed image with data used to reconstruct the image, comprising:
a plurality of detectors that detect electron-positron annihilation events;

a coincident detector that identifies pairs of substantially simultaneous coincident events within the electron-positron annihilation events;

a line of response processor that processes the events and identifies lines of responses that connect events within each coincident event pair; and one or more processors programmed to:
- group the lines of response into temporally contiguous groups;
- reconstructing at least a portion of the lines of response corresponding at least to a region of interest into an intermediate image;
- estimate a location of the region of interest in the intermediate image reconstructed from the lines of response in each group;
- shift the lines of response in each group such that the location of the region of interest in each group is aligned to generate the motion corrected lines of response; and
- reconstruct the shifted lines of response into an image of the field of view which at least the region of interest is motion corrected.

26. The medical imaging system as set forth in claim 25, wherein the lines of response are list mode data.

27. The medical imaging system as set forth in claim 25 wherein the one or more processors are further programmed to:
- reconstruct the lines of response unshifted into a motion blurred image; and
- replace the region of interest in the motion blurred image with the motion corrected region of interest.

28. A non-transitory computer-readable medium carrying software which controls one or more processors to perform the steps of:
- generating a plurality of intermediate regions of interest images from an motion-blurred region of interest for a number of short time frames;
- adjusting, for each of the plurality of intermediate regions of interest images, a voxel value for one or more voxels that reside inside a region of interest and that intersect a corresponding line of response;
- computing a center for each of the intermediate regions of interest images;
- combining the individual centers to compute an aggregate center for a full time range of an acquisition;
- computing a difference between each center and the aggregated center;
- computing a motion correction translation vector based on the differences;
- correcting data corresponding to the region of interest for motion by shifting lines of response in the data by an amount given by the motion correction translation vector; and
- reconstructing a motion-corrected image corresponding to the region of interest with the corrected data.

29. A medical imaging system that corrects motion in a reconstructed image with data used to reconstruct the image, comprising:

a coincident detector that identifies pairs of substantially simultaneous coincident electron-positron annihilation events; and one or more processors programmed to:
- identify a line of response corresponding to each coincident event pair;
- generate a plurality of intermediate images from at least one region of interest for a number of short time frames;
- compute a center of the region of interest in each of the intermediate images;
- calculate for each time frame a vector which moves the center of each region of interest to a common location;
- shift the lines of response for each time frame with the corresponding vector;
- reconstruct the shifted lines of response into a diagnostic image.

30. A method of forming a motion corrected image, comprising:
- defining a region of interest within an uncorrected image;
- generating a plurality of intermediate images from the region of interest for a number of short time frames;
- adjusting, for each of the plurality of intermediate images, a voxel value for one or more voxels that reside inside the region of interest and that intersect a corresponding line of response;
- computing a center of mass for each of the intermediate images;
- combining the individual center of masses to compute the center of mass of the region of interest for a full time range of an acquisition; and
- correcting the region of interest for differences caused by local motion by calculating a translation vector based on changes in a center of mass of the region of interest.

31. The method as set forth in claim 30, further including:
- computing a difference between the individual center of masses and the center of mass of the region of interest; and
- computing the translation vector based on the differences.

32. The method as set forth in claim 30, wherein the region of interest is localized to anatomy within a field of view.

* * * * *